Dec. 16, 1969 C. G. KLEHM Plant Pat. 2,952
PEONY
Filed May 22, 1968
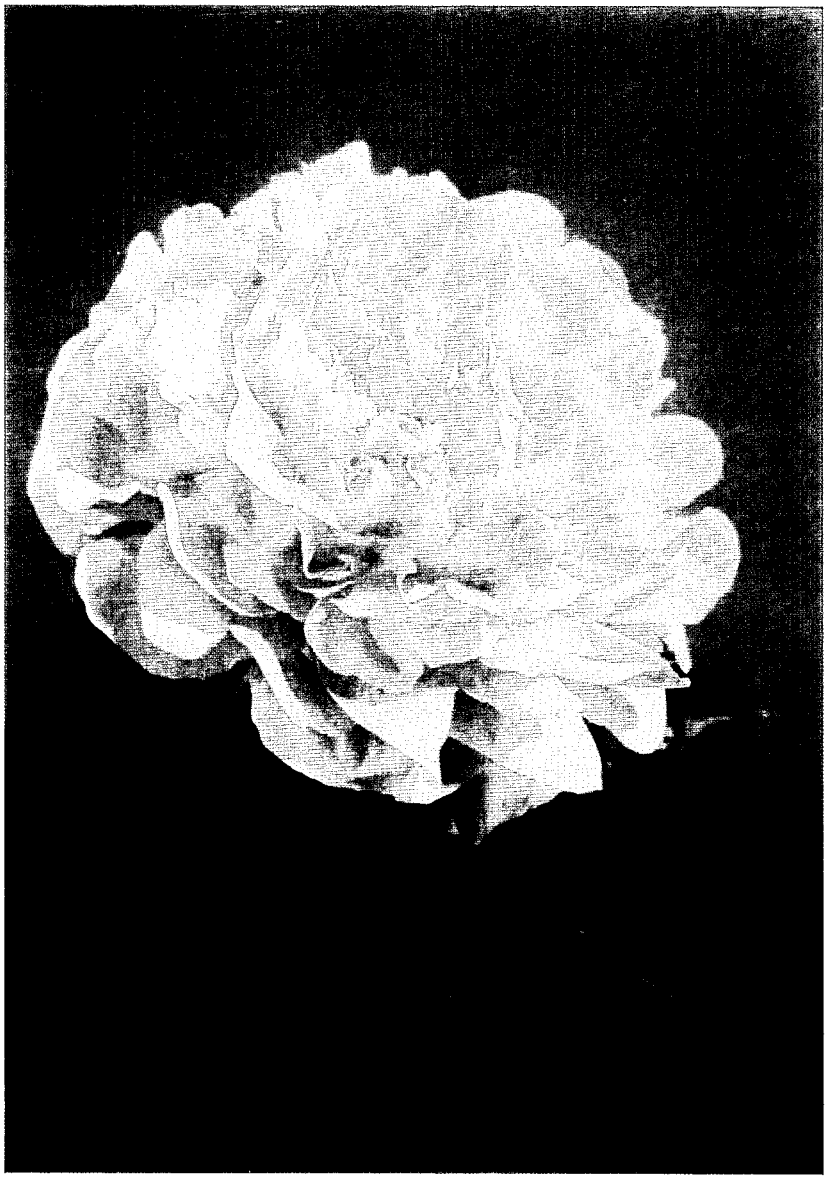
Inventor
Carl G. Klehm
By Hofgren, Wegner,
Allen, Stellman & McCord
Atty's

United States Patent Office

Plant Pat. 2,952
Patented Dec. 16, 1969

2,952
PEONY PLANT

Carl G. Klehm, 3 E. Algonquin Road,
Arlington Heights, Ill. 60005

Filed May 22, 1968, Ser. No. 731,341
Int. Cl. A01b *5/02*
U.S. Cl. Plt.—68 1 Claim

The present invention relates to a new variety of peony plant belonging to genus Paeonia and species *lactiflora*. It is especially unique because of its immense flower size, unusual flat flower form, and pleasing cameo color. The robustness of the plant, its willingness to grow and thrive under a wide variance of microclimatic conditions, and its lush dark green foliage make it a welcome addition to any landscape setting.

This plant was originated by me at my nursery in Arlington Heights, Ill., from a cross between an unnamed seedling produced in my nursery, the pollen parent, and Mons. Jules Elie, the seed parent (both non-patented). The process of hybridization was done by hand pollination and the mode of reproduction was asexual root division. Of the thousands of seedlings developed by this particular cross, this plant was selected as being most unique. Since the first bloom on the first plant, this variety has been under watchful observation for fifteen years.

This variety derives its heterosis from the best growth qualities of each parent. Its unusually flat dinner-plate-like flower is not evident in either parent, so this characteristic must be credited to the combination of hidden genes from both parents. The immense size of the flower is derived from its pollen parent, an unnamed seedling developed in my nursery. The beautiful cameo petal color is characteristic of its seed parent, Mons. Jules Elie.

It is a marked characteristic of this flower that its guard petals are over 2" in width. This, along with the ten-inch platelike flower form make this plant one-of-a-kind among other peony varieties. The bloom has no stamens, tiny rudimentary central carpels, and an eye-catching, pleasing cameo-pink blossom color. This color is clean and shows up well against the abundant dark green foliage. The stems are long, making the plant useful for cutflower arrangements.

This variety is especially recommended and suitable for growing as a garden attraction in the home landscape plan because of its exceptional flower size, form and pleasing petal color.

The accompanying drawing shows a view of an individual flower, in color as nearly true as reasonably possible in a color illustration of this character.

As a convenient summary, the following detailed description of this new peony plant is given with color terminology generally in accordance with Kornerup and Wanscher's 1961 edition of Reinhold Color Atlas.

Parentage:

*Seed parent.*—Mons. Jules Elie, from which the plant derives its cameo color, part of its heterosis and part of its platelike flower form.

*Pollen parent.*—An unnamed seedling developed in my nursery from which the plant derives its pleasing color and parts of its heterosis and flower form.

FLOWER

Blooming habit: Annually.

Bud:

*Size.*—Huge 1½" to 2" in diameter.
*Form.*—Smooth, even and round.
*Color.*—Cameo pink.
*Sepals.*—Smooth green wrapped tightly around bud.
*Calyx.*—Polysepalous.
*Peduncle.*—None.
*Opening.*—Unfailing opening qualities—dependable performer.

Bloom:

*Size.*—Huge average size, fully expanded 10 inches.
*Borne.*—Singly, one main terminal bud per stem with 0 to 3 axillary buds.
*Form.*—Flat rose type with 2–4 rows of outer guard petals.
*Petalage.*—Double.
*Color.*—Cameo pink 13A2–3
*Variegations.*—None.
*Discolorations.*—None.

Petals:

*Texture.*—Thick—affected little by wet and hot weather.
*Appearance.*—Silky but bold because of size.
*Form.*—Smooth, slightly cupped.
*Arrangement.*—Imbricated—many petaloids in center.
*Persistence.*—Good.
*Fragrance.*—Mild.
*Lastingness.*—Unusually long.

Genital organs:

*Stamens, anthers and filaments.*—None.
*Pollen.*—None.
*Styles.*—Rudimentary.
*Stigmas.*—Rudimentary.
*Ovaries.*—Rudimentary.

Fruit: None.

PLANT

Form: Herbaceous bush.
Growth: Vigorous, strong.
Foliage:

*Leaflets.*—Five to seven.
*Size.*—Large.
*Quantity.*—Normal.
*Color.*—Lush dark green 28F8.
*Shape.*—Elliptically acute.
*Stem.*—Long, approximately 33" length.
*Texture.*—Pronounced veins—dorsal, glossy ventral smooth.
*Edge.*—Smooth.
*Serration.*—None.
*Leaf stem color.*—Normal.
*Stipules.*—None.
*Disease resistance.*—Good resistance to leaf blotch and fungus diseases as observed for fifteen years.

I claim:

1. A new and distinct variety of peony plant especially characterized by its flower size, form and color.

No references cited.

ROBERT E. BAGWILL, Primary Examiner